United States Patent [19]

Hänssle et al.

[11] Patent Number: 4,513,157

[45] Date of Patent: Apr. 23, 1985

[54] ISOMERIZATION OF ISOLATED DOUBLE BONDS TO CONJUGATED DOUBLE BONDS IN OPTIONALLY SUBSTITUTED CYCLOOCTADIENES

[75] Inventors: Peter Hänssle, Haltern; Wolfgang Zaar, Marl, both of Fed. Rep. of Germany

[73] Assignee: Chemische Werke Huels, AG, Marl, Fed. Rep. of Germany

[21] Appl. No.: 623,695

[22] Filed: Jun. 22, 1984

[30] Foreign Application Priority Data

Jul. 13, 1983 [DE]  Fed. Rep. of Germany ....... 3325268

[51] Int. Cl.$^3$ ............................................... C07C 5/24
[52] U.S. Cl. ................... 585/378; 585/665; 585/669; 585/670
[58] Field of Search ............... 585/378, 665, 664, 669, 585/670

[56] References Cited

U.S. PATENT DOCUMENTS 3,507,928  4/1970  Rinehart ............................. 585/378
4,434,310  2/1984  Kampf ................................ 585/377

FOREIGN PATENT DOCUMENTS 2519627   7/1983  France ............................... 585/665
973850   10/1964  United Kingdom ................ 585/377

Primary Examiner—Delbert E. Gantz
Assistant Examiner—A. Pal
Attorney, Agent, or Firm—Millen & White

[57]   ABSTRACT

In the isomerization of isolated double bonds to conjugated double bonds in optionally substituted cyclooctadienes, the isomerization catalyst comprises: (a) a transition metal compound of the formula $Me(OR^1)_4$, wherein Me is Ti, Zr, or Hf, and $R^1$ is $C_{1-4}$ alkyl, and (b) an organoaluminum compound of the general formula $AlR^2{}_{3-n}X_n$, wherein $R^2$ is $C_{1-4}$ alkyl, n is 0, 1, 2, or a fraction between 1 and 2, and X is halogen or, if n is 1, also hydrogen; the molar ratio of (a):(b) being in the range from 0.1 to 1:1, the catalyst having prolonged activity and the isomerization being conducted at a temperature of 50°–200° C.

17 Claims, No Drawings

ISOMERIZATION OF ISOLATED DOUBLE BONDS TO CONJUGATED DOUBLE BONDS IN OPTIONALLY SUBSTITUTED CYCLOOCTADIENES

BACKGROUND OF THE INVENTION

This invention relates to the catalytic isomerization of isolated double bonds to conjugated double bonds in optionally substituted octadienes.

The individual, isomeric forms of unconjugated cyclooctadienes such as, for example, cis,cis-1,4- and cis,cis-1,5-cyclooctadiene, are valuable starting materials for various syntheses. In some cases however, for example, for polymerizations or epoxidations, it is desirable to have the double bonds present in the conjugated form. Furthermore, optionally substituted cyclooctadienes with conjugated double bonds have the advantage that they can be hydrogenated to the corresponding monoenes in a single-step reaction without any appreciable formation of saturated by-products.

All methods heretofore known for the isomerization of isolated to conjugated double bonds in optionally substituted cyclooctadienes, however, are more or less hampered by deficiencies. Thus, in the process according to U.S. Pat. No. 3,398,205 wherein iron pentacarbonyl is primarily used as the catalyst, problems are encountered in the clean separation of the isomerized product on account of the volatility of the catalyst. In the method disclosed in U.S. Pat. No. 3,767,716, wherein the catalyst is alkali metal hydroxide applied together with an alkali metal or aluminum oxide, there is a different drawback. Here, the catalysts are difficult to handle technically since they are very sensitive to air and entail a certain risk. Finally, in the process of U.S. Pat. No. 3,124,621 wherein isomerization is conducted using alkali or alkaline earth metal amides in the presence of ammonia or amines as the solvent, relatively high catalyst concentrations must be employed to attain an industrially interesting degree of isomerization. An additional disadvantage in this process is the necessity of using relatively large quantities of a solvent.

Although the process according to U.S. Pat. No. 4,434,310 has managed to overcome disadvantages of the above-described methods, the isomerization catalyst employed in said process suffers an appreciable loss of activity upon repeated usage.

OBJECTS OF THE INVENTION

It is therefore an object of this invention to provide a process for the isomerization of isolated double bonds to conjugated double bonds in optionally substituted cyclooctadienes wherein the catalyst employed can be reused repeatedly without appreciable loss of activity, and wherein the reaction periods are relatively brief.

Upon further study of the specification and appended claims, further objects and advantages of this invention will become apparent to those skilled in the art.

SUMMARY OF THE INVENTION

To attain these objects a process is provided wherein the isomerization catalyst comprises or consists essentially of: (a) a transition metal compound of the formula $Me(OR^1)_4$, wherein Me is Ti, Zr, or Hf, and $R^1$ is $C_{1-4}$ alkyl, and (b) an organoaluminum compound of the formula $AlR^2{}_{3-n}X_n$, wherein $R^2$ is $C_{1-4}$ alkyl, n is 0, 1, 2 or a fraction between 1 and 2, and X is halogen, or when n is 1, X is halogen or hydrogen; the molar ratio of (a):(b) being from 0.1:1 to 1:1.

DETAILED DISCUSSION

Cyclooctadienes suitable for use in this invention include not only the possible unsubstituted isomers, but also the counterparts which carry alkyl groups, preferably of up to 5 carbon atoms each. Cyclooctadienes with isolated double bonds include but are not limited to, for example, cis,cis-1,5-cyclooctadiene (COD-1,5); cis,cis-3-methyl-1,5-cyclooctadiene; cis,cis-3,7-diethyl-1,5-cyclooctadiene; cis,cis-3,4,8-tri-n-propyl-1,5-cyclooctadiene; cis,cis-3,4,7,8-tetra-n-pentyl-1,5-cyclooctadiene; cis,cis-1,2,3,4,5,6,7,8-octamethyl-1,5-cyclooctadiene; cis,trans-1,5-cyclooctadiene; cis,trans-3-n-butyl-1,5-cyclooctadiene; cis,trans-4,8-di-n-pentyl-1,5-cyclooctadiene; cis,trans-3,4-dimethyl-1,5-cyclooctadiene; cis,trans-1,2,5,6-tetraisopropyl-1,5-cyclooctadiene; cis,trans-8-tert-butyl-1,5-cyclooctadiene; cis-trans-1,2,3,4,5,6,7,7,8,8-deca-n-pentyl-1,5-cyclooctadiene; cis,trans-1,2-diethyl-1,5-cyclooctadiene; cis,cis-1,2-dimethyl-1,4-cyclooctadiene; cis,cis-3-ethyl-1,4-cyclooctadiene; cis,cis-3,8,8-tri-n-propyl-1,4-cyclooctadiene; cis,cis-1,2,4,5,6,6,7,7,8,8-decamethyl-1,4-cyclooctadiene; cis,cis-1,4-cyclooctadiene; cis,cis-1,2,3,3-tetra-n-butyl-1,4-cyclooctadiene; cis,cis-1,2,4,5-tetra-n-pentyl-1,4-cyclooctadiene; cis,cis-1,2,3,3,4,5,6,7,8-nona-n-propyl-1,4-cyclooctadiene; cis,trans-1,2,7,7-tetramethyl-1,4-cyclooctadiene, cis,trans-6,6,7,7,8,8-hexa-n-butyl-1,4-cyclooctadiene; cis,trans-1,2,3,4-tetra-n-pentyl-1,4-cyclooctadiene; cis,trans-1,2,4,5,6,6,8-heptaethyl-1,4-cyclooctadiene; cis,trans-8-tert-butyl-1,4-cyclooctadiene; cis,trans-3,3-di-sec-pentyl-1,4-cyclooctadiene; cis,trans-3,3,7,8-tetraethyl-1,4-cyclooctadiene; cis,trans-1,2,3,3,4,5,6,7,7-nona-n-propyl-1,4-cyclooctadiene; and cis,trans-1,4-cyclooctadiene.

With respect to the catalysts employed in this invention, examples of catalyst component (a) include but are not limited to: $Ti(OCH_3)_4$, $Ti(OC_2H_5)_4$, $Ti(O\!-\!n\!-\!C_3H_7)_4$, $Ti(O\!-\!i\!-\!C_3H_7)_4$, $Ti(O\!-\!n\!-\!C_4H_9)_4$, $Ti(O\!-\!sec\!-\!C_4H_9)_4$, and $Ti(O\!-\!tert\!-\!C_4H_9)_4$, as well as the corresponding zirconium and hafnium compounds, and the Ti, Zr and Hf alcoholates with mixed alkoxy groups. The symmetric alcoholates of titanium are preferred.

Examples of catalyst component (b) include but are not limited to: $Al(CH_3)_3$, $Al(C_2H_5)_3$, $Al(n\!-\!C_3H_7)_3$, $Al(i\!-\!C_3H_7)_3$, $Al(n\!-\!C_4H_9)_3$, $Al(sec\!-\!C_4H_9)_3$, $(CH_3)_2AlH$, $(C_2H_5)_2AlH$, $(n\!-\!C_3H_7)_2AlH$, $(i\!-\!C_3H_7)_2AlH$, $(n\!-\!C_4H_9)_2AlH$, $(sec\!-\!C_4H_9)_2AlH$, $(C_2H_5)_2AlCl$, $C_2H_5AlCl_2$, $(C_2H_5)_3Al_2Cl_3$, $(C_2H_5)_2AlBr$, $C_2H_5AlBr_2$, and $(C_2H_5)_3Al_2Br_3$. Triethylaluminum is preferred from the group of alkyl aluminum compounds, and di-iso-butylaluminum hydride is preferred from the group of the dialkyl aluminum hydrides.

Preferred combinations of (a) and (b) are:

(iso—$C_4H_9$)$_2$AlH/Ti(O—n—$C_4H_9$)$_4$

Al($C_2H_5$)$_3$/Ti(O—n—$C_4H_9$)$_4$ (iso—$C_4H_9$)$_2$AlH/Zr(O—i—$C_3H_7$)$_4$.

The molar ratio of (a):(b) generally ranges from 0.1:1 to 1:1, preferably 0.2:1 to 1:1, and especially preferably 0.4:1 to 1:1.

The catalyst is, of course, employed in isomerizing amounts. Thus, the molar ratio of the cyclooctadiene to be isomerized to the organoaluminum compound can be varied widely, considerations being, e.g., a balance between the space-time yield and the cost of catalyst and equipment. In general, this ratio is higher than 1:1 and lower than 1,000:1, ranging preferably between 10:1 and 100:1.

Isomerization is generally performed in a temperature range from 50° to 200° C., preferably in a range from 80° to 160° C.

The reaction times are generally between 5 minutes and 24 hours, depending on the conditions selected (catalyst concentration, ratio of catalyst components, temperature).

The addition of a solvent is optional, but not a requirement in the process of this invention. Suitable solvents which, of course, must be substantially anhydrous, just as the cyclooctadiene employed, (e.g., less than 10 ppm $H_2O$), include but are not limited to, for example, aliphatic and aromatic hydrocarbons, e.g., cyclohexane and toluene.

In general, the process of this invention is conducted at atmospheric pressure. However, if the isomerization temperature is above the boiling point of the cyclooctadiene to be isomerized, and/or above the mixed boiling point resulting from the cyclooctadiene with isolated double bonds and the cyclooctadiene with conjugated double bonds, and/or above the boiling point of the optionally employed solvent, then appropriate superatmospheric pressures are employed, e.g., by use of an autoclave.

A resultant reaction batch is generally worked up by distillation. In an optional embodiment of this invention when using cis,cis-1,5-cyclooctadiene, for example, the isomerized product, cis,cis-1,3-cyclooctadiene (COD-1,3), is continuously removed by distillation (up to a certain point of catalyst exhaustion) and is replaced by fresh cis,cis-1,5-cyclooctadiene.

Since the cis,cis-configuration represents the most stable form of cyclooctadienes with conjugated double bonds, the resultant conjugated diene is a cis,cis-1,3-cyclooctadiene. The basic skeleton thus has the following formula

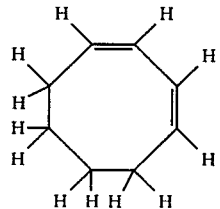

Cyclooctadienes with conjugated double bonds, preferably cis,cis-1,3-cyclooctadiene, can be utilized, inter alia, for the stabilization of copolymers of unsaturated nitriles and monovinylidene aromatics against discoloring by heat and/or aging as described in U.S. Pat. No. 3,444,126, incorporated by reference herein. Furthermore they can be converted advantageously into the corresponding monoenes—as mentioned above—by one-stage hydrogenation. These monoenes are used primarily for the production of polymers with the use of a so-called metathetical catalyst. This catalyst is generally extremely sensitive against impurities, such as, for example, nitrogen-containing components. For this reason, the process of this invention has an advantage over the prior art processes wherein isomerization carried out with nitrogen-containing catalysts provides a source of contamination for the metathetical catalysts. See R. Streck, Chemiker Zeitung 99, 397–413 (1975), especially p. 399.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The analytical characterizing data were determined by gas chromatography.

EXAMPLE 1

In a three-necked flask, 80 millimoles of diisobutyl aluminum hydride (DIBAL-H) and 8 mmol of titanium tetra-n-butylate [Ti(O—n—$C_4H_9$)$_4$] are added to 800 mmol of 1,5-cyclooctadiene (COD-1,5). The mixture is heated to reflux under argon and maintained in this condition for several hours. By means of a syringe, a 5 ml sample is withdrawn every half hour (h), and this sample is introduced into a mixture of 50 ml of ether and 10 ml of methanol. (Zero time starts 20 minutes after combining COD-1,5, DIBAL-H, [Ti(O—n—$C_4H_9$)$_4$] and subsequent heating.) Then 5 ml of 1N hydrochloric acid is added to dissolve the thus-produced aluminum methylate. The organic phase is separated and washed with water. Neutralization is effected with 1% strength sodium carbonate solution. Then the mixture is washed once more with water. The ether is withdrawn and the residue examined by gas chromatography. The results are compiled in Table 1.

Insofar as not as yet mentioned hereinabove, the abbreviations mean:
BCO: bicyclo(3.3.0)octene-2
COD-1,4: 1,4-cyclooctadiene
COD-1,3: 1,3-cyclooctadiene.

TABLE 1

| Time (h) | 0.5 | 1 | 1.5 | 2 | 2.5 |
|---|---|---|---|---|---|
| BCO (%) | 2.2 | 2.3 | 2.4 | 2.4 | 2.4 |
| COD-1,5 (%) | 4.8 | 3.1 | 2.1 | 1.3 | 1.1 |
| COD-1,4 (%) | 5.8 | 3.7 | 2.8 | 2.2 | 1.6 |
| COD-1,3 (%) | 68.3 | 70.2 | 67.3 | 72.4 | 69.6 |
| Cyclooctene (%) | 12.7 | 12.6 | 13.4 | 10.3 | 10.1 |
| High-Boiling Compounds (%) | 6.2 | 8.1 | 12.0 | 11.4 | 15.2 |

EXAMPLE 2

The procedure of Example 1 is followed, except that 40 mmol of DIBAL-H is used in place of 80 mmol.

The results are summarized in Table 2:

TABLE 2

| Time (h) | 0.5 | 1 | 1.5 | 2 | 2.5 |
|---|---|---|---|---|---|
| BCO (%) | 1 | 1.6 | 1.8 | 2.0 | 1.9 |
| COD-1,5 (%) | 0.5 | 0.3 | 0.3 | 0.3 | 0.3 |
| COD-1,4 (%) | 1.3 | 1.3 | 1.1 | 1.1 | 1.2 |
| COD-1,3 (%) | 87.7 | 89.9 | 90.8 | 90.0 | 90.9 |
| Cyclooctene (%) | 4.3 | 4.5 | 4.5 | 4.7 | 4.4 |
| High-Boiling Compounds (%) | 5.2 | 2.4 | 1.5 | 1.9 | 1.3 |

EXAMPLE 3

The procedure is conducted as set out in Example 1, but using 40 mmol of triethylaluminum instead of 80 mmol of DIBAL-H.

The results are compiled in Table 3:

TABLE 3

| Time (h) | 0.5 | 1 | 1.5 | 2 | 2.5 |
|---|---|---|---|---|---|
| BCO (%) | 1.0 | 1.3 | 1.5 | 1.5 | 1.6 |
| COD-1,5 (%) | 0.5 | 0.3 | 0.2 | 0.2 | 0.2 |
| COD-1,4 (%) | 1.8 | 1.0 | 1.0 | 1.0 | 1.0 |
| COD-1,3 (%) | 91.9 | 93.4 | 93.2 | 92.0 | 92.3 |
| Cyclooctene (%) | 1.6 | 1.8 | 1.9 | 2.0 | 2.0 |
| High-Boiling Compounds (%) | 3.2 | 2.2 | 2.2 | 3.3 | 2.9 |

EXAMPLE 4

The process is carried out as described in Example 1, but employing 40 mmol of DIBAL-H and 8 mmol of zirconium tetraisopropylate instead of 80 mmol of DIBAL-H and 8 mmol of $Ti(O-n-C_4H_9)_4$.

The results are summarized in Table 4:

TABLE 4

| Time (h) | 0.5 | 1 | 1.5 | 2 | 2.5 |
|---|---|---|---|---|---|
| BCO (%) | 0.7 | 1.7 | 2.1 | 2.3 | 2.5 |
| COD-1,5 (%) | 13.3 | 0.8 | 0.3 | 0.2 | 0.2 |
| COD-1,4 (%) | 16.2 | 1.6 | 1.1 | 0.9 | 0.9 |
| COD-1,3 (%) | 63.1 | 85.7 | 86.4 | 85.5 | 85.2 |
| Cyclooctene (%) | 3.5 | 5.3 | 5.8 | 6.0 | 6.1 |
| High-Boiling Compounds (%) | 3.2 | 4.9 | 4.3 | 5.1 | 5.1 |

EXAMPLE 5

The procedure of Example 1 is followed, but using 20 mmol instead of 80 mmol of DIBAL-H.

The results are shown in Table 5:

TABLE 5

| Time (h) | 0.5 | 1 | 1.5 | 2 | 2.5 |
|---|---|---|---|---|---|
| BCO (%) | 0.4 | 0.5 | 0.6 | 0.6 | 0.6 |
| COD-1,5 (%) | 3.0 | 0.5 | 0.4 | 0.2 | 0.2 |
| COD-1,4 (%) | 3.4 | 1.2 | 1.1 | 1.1 | 1.0 |
| COD-1,3 (%) | 91.5 | 96.1 | 96.4 | 96.3 | 96.3 |
| Cyclooctene (%) | 1.4 | 1.5 | 1.5 | 1.6 | 1.6 |
| High-Boiling Compounds (%) | 0.3 | 0.2 | 0 | 0.2 | 0.3 |

EXAMPLE 6

Under argon, 2.45 moles of COD-1,5 is combined in a three-necked flask with 40 millimoles of titanium tetrabutylate, heated to 120° C., and then mixed dropwise with 100 millimoles of triethylaluminum in 200 ml (1.6 moles) of COD-1,5. During this step, slight cooling is necessary on account of the exothermic reaction, in order to maintain the temperature at about 120° C. After adding the entire amount of COD-1,5 (zero hour), samples of respectively 5 ml are withdrawn after 5, 15, and 30 minutes and worked up as described in Example 1. Subsequently, the samples are analyzed by gas chromatography. The liquid in the flask is distilled off at 120° C. and under 100 mbar. Then the flask is cooled and expanded under argon. The remaining catalyst mixture is again combined with 500 ml (4.2 mol) of COD-1,5. Then the flask is again heated to 120° C., and 5 ml samples are once more taken 5, 15, and 30 minutes after reaching this temperature. The samples are analyzed as set forth above. Then the volatile components of the reaction flask are again removed by distillation, and the residue also combined with 500 ml of COD-1,5.

In this way, the catalyst made up of triethylaluminum and titanium tetrabutylate was reused seven times—without additional metered feeding of fresh catalyst components.

The results of the individual experiments are compiled in Table 6:

TABLE 6

| Isomeri-zation | Time (min) | Olefin Content (%) | | |
|---|---|---|---|---|
| | | COD-1,3 | COD-1,4 | COD-1,5 |
| I | 5 | 86.6 | 5.9 | 6.0 |
| | 15 | 96.1 | 0.7 | 0.7 |
| | 30 | 96.6 | 0.5 | 0.4 |
| II | 5 | 82.1 | 7.6 | 8.4 |
| | 15 | 85.8 | 5.2 | 7.0 |
| | 30 | 97.0 | 0.5 | 0.4 |
| III | 5 | 80.4 | 7.8 | 10.2 |
| | 15 | 85.0 | 5.3 | 7.9 |
| | 30 | 95.7 | 1.0 | 1.3 |
| IV | 5 | 83.4 | 7.6 | 7.3 |
| | 15 | 87.9 | 4.6 | 5.5 |
| | 30 | 93.4 | 2.1 | 2.5 |
| V | 5 | 75.6 | 11.2 | 12.0 |
| | 15 | 82.0 | 7.6 | 8.4 |
| | 30 | 94.2 | 1.8 | 1.7 |
| VI | 5 | 56.1 | 20.0 | 22.4 |
| | 15 | 70.5 | 14.0 | 14.0 |
| | 30 | 92.0 | 3.0 | 3.2 |
| VII | 5 | 15.1 | 11.4 | 72.0 |
| | 15 | 30.7 | 27.9 | 39.4 |
| | 30 | 70.9 | 13.5 | 13.5 |

After termination of the experiments and after removal of distillation at 120° C. and under 100 mbar, 49.5 g of residue remained in the reaction flask. This corresponds—after deducting the amount of the catalyst by calculation—to a proportion of high-boiling compounds of about 1%, based on COD-1,5 utilized.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the isomerization of isolated double bonds to conjugated double bonds in optionally substituted cyclooctadienes using an isomerization catalyst, optionally in the presence of a solvent, the improvement wherein said isomerization catalyst comprises:
    (a) a transition metal compound of the formula Me-$(OR^1)_4$, wherein Me is Ti, Zr, or Hf, and $R^1$ and $C_{1-4}$ alkyl; and
    (b) an organoaluminum compound of the formula $AlR^2{}_{3-n}X_n$, wherein $R^2$ is $C_{1-4}$ alkyl, n is 0, 1, 2 or a fraction between 1 and 2, and X is halogen, or when n is 1, X is halogen or hydrogen;
    the molar ratio of (a):(b) being from 0.1:1 to 1:1.

2. A process according to claim 1, wherein catalyst component (a) is a titanium alcoholate and catalyst component (b) is a trialkyl aluminum compound or a dialkyl aluminum hydride.

3. A process according to claim 2, wherein the isomerization is conducted at a temperature of 50°–200° C.

4. A process according to claim 1, wherein the isomerization is conducted at a temperature of 80°–160° C.

5. A process according to claim 1, wherein the molar ratio (a):(b) is 0.2:1 to 1:1.

6. A process according to claim 1, wherein the molar ratio (a):(b) is 0,4:1 to 1:1.

7. A process according to claim 1, wherein the starting cyclooctadiene containing isolated bonds is cis,cis-1,5-cyclooctadiene, cis,cis-3-methyl-1,5-cyclooctadiene, cis,cis-3,7-diethyl-1,5-cyclooctadiene, cis,cis-3,4,8-tri-n-propyl-1,5-cyclooctadiene, cis,cis-3,4,7,8-tetra-n-pentyl-1,5-cyclooctadiene, cis,cis-1,2,3,4,5,6,7,8-octamethyl-1,5-cyclooctadiene, cis,trans-1,5-cyclooctadiene, cis,trans-3-n-butyl-1,5-cyclooctadiene, cis,trans-4,8-di-n-pentyl-1,5-cyclooctadiene, cis,trans-3,4-dimethyl-1,5-cyclooctadiene, cis,trans-1,2,5,6-tetraisopropyl-1,5-cyclooctadiene, cis,trans-8-tert-butyl-1,5-cyclooctadiene, cis,trans-1,2,3,4,5,6,7,7,8,8-deca-n-pentyl-1,5-cyclooctadiene, cis,trans-1,2-diethyl-1,5-cyclooctadiene, cis,cis-1,2-dimethyl-1,4-cyclooctadiene, cis,cis-3-ethyl-1,4-cyclooctadiene, cis,cis-3,8,8-tri-n-propyl-1,4-cyclooctadiene, cis,cis-1,4-cyclooctadiene, cis,cis-1,2,3,3-tetra-n-butyl-1,4-cyclooctadiene, cis,cis-1,2,4,5-tetra-n-pentyl-1,4-cyclooctadiene, cis,cis-1,2,3,3,4,5,6,7,8-nona-n-propyl-1,4-cyclooctadiene, cis,trans-1,2,7,7-tetramethyl-1,4-cyclooctadiene, cis,trans-6,6,7,7,8,8-hexa-n-butyl-1,4-cyclooctadiene, cis,trans-1,2,3,4-tetra-n-pentyl-1,4-cyclooctadiene, cis,trans-1,2,4,5,6,6,8-heptaethyl-1,4-cyclooctadiene, cis,trans-8-tert-butyl-1,4-cyclooctadiene, cis,trans-3,3-di-sec-pentyl-1,4-cyclooctadiene, cis,trans-3,3,7,8-tetraethyl-1,4-cyclooctadiene, cis,trans-1,2,3,3,4,5,6,7,7-nona-n-propyl-1,4-cyclooctadiene, or cis,trans-1,4-cyclooctadiene.

8. A process according to claim 6, wherein the starting cyclooctadiene containing isolated bonds is cis,cis-1,5-cyclooctadiene.

9. A process according to claim 2, wherein catalyst component (a) is titanium butylate and component (b) triethyl aluminum or di-iso-butyl aluminum hydride.

10. A process according to claim 1, wherein the molar ratio of the optionally substituted cyclooctadiene to component (b) is from 1:1 to 1,000:1.

11. A process according to claim 1, wherein the molar ratio of the optionally substituted cyclooctadiene to component (b) is from 10:1 to 100:1.

12. A process according to claim 1, wherein component (b) is $Al(CH_3)_3$, $Al(C_2H_5)_3$, $Al(n-C_3H_7)_3$, $Al(i-C_3H_7)_3$, $Al(n-C_4H_9)_3$, $Al(sec-C_4H_9)_3$, $(CH_3)_2AlH$, $(C_2H_5)_2AlH$, $(n-C_3H_7)_2AlH$, $(i-C_3H_7)_2AlH$, $(n-C_4H_9)_2AlH$, $(iso-C_4H_9)_2AlH$, $(C_2H_5)_2AlCl$, $C_2H_5AlCl_2$, $(C_2H_5)_3Al_2Cl_3$, $(C_2H_5)_2AlBr$, $C_2H_5AlBr_2$, or $(C_2H_5)_3Al_2Br_3$.

13. A process according to claim 1, wherein component (a) is $Ti(OCH_3)_4$, $Ti(OC_2H_5)_4$, $Ti(O-n-C_3H_7)_4$, $Ti(O-i-C_3H_7)_4$, $Ti(O-n-C_4H_9)_4$, $Ti(O-sec-C_4H_9)_4$, or $Ti(O-tert-C_4H_9)_4$.

14. A process according to claim 12, wherein component (a) is $Ti(OCH_3)_4$, $Ti(OC_2H_5)_4$, $Ti(O-n-C_3H_7)_4$, $Ti(O-i-C_3H_7)_4$, $Ti(O-n-C_4H_9)_4$, $Ti(O-sec-C_4H_9)_4$, or $Ti(O-tert-C_4H_9)_4$.

15. A process according to claim 1 carried out in a reaction-compatible solvent.

16. A process according to claim 1 carried out in an autoclave.

17. A process according to claim 1 carried out in the absence of a solvent.

* * * * *